United States Patent
Teal (10) Patent No.: US 9,876,339 B2
(45) Date of Patent: Jan. 23, 2018

(54) THERMAL SLEEVE WITH INTEGRAL POSITIONING MEMBER, ASSEMBLY THEREWITH AND METHOD OF CONSTRUCTION THEREOF

(71) Applicant: Federal-Mogul Powertrain, LLC, Southfield, MI (US)

(72) Inventor: Jimmy E. Teal, Mohnton, PA (US)

(73) Assignee: Federal-Mogul Powertrain, LLC, Southfield, MI (US)

( * ) Notice: Subject to any disclaimer, the term of this patent is extended or adjusted under 35 U.S.C. 154(b) by 0 days.

(21) Appl. No.: 15/202,132

(22) Filed: Jul. 5, 2016

(65) Prior Publication Data
US 2017/0012417 A1    Jan. 12, 2017

Related U.S. Application Data (60) Provisional application No. 62/189,097, filed on Jul. 6, 2015.

(51) Int. Cl.
*H02G 3/04* (2006.01)
*G01N 27/407* (2006.01)

(52) U.S. Cl.
CPC ....... *H02G 3/0412* (2013.01); *G01N 27/4078* (2013.01); *H02G 3/0481* (2013.01)

(58) Field of Classification Search
USPC .................................................. 174/92, 74 A
See application file for complete search history.

(56) References Cited

U.S. PATENT DOCUMENTS

| 2,980,144 | A |   | 4/1961 | Edwards, Jr. et al. |
| 4,016,356 | A | * | 4/1977 | McLoughlin ....... B29C 61/0616 138/139 |
| 4,142,592 | A | * | 3/1979 | Brusselmans ...... H02G 15/1806 156/49 |

(Continued)

FOREIGN PATENT DOCUMENTS

| EP | 0041388 A1 | 12/1981 |
| EP | 0624790 A1 | 11/1994 |

(Continued)

OTHER PUBLICATIONS

International Search Report, dated Oct. 11, 2016 (PCT/US2016/041020).

*Primary Examiner* — William H Mayo, III
*Assistant Examiner* — Krystal Robinson
(74) *Attorney, Agent, or Firm* — Robert L. Stearns; Dickinson Wright, PLLC (57) ABSTRACT

A thermal sleeve for protecting an electronic member connected to a wiring harness, assembly therewith and method of construction are provided. The thermal sleeve includes a tubular heat-settable nonwoven inner layer having a generally cylindrical portion and an outer surface extending along a longitudinal central axis between opposite open ends. A reflective outer layer is disposed about the outer surface. At least one finger of the heat-settable nonwoven inner layer extends radially inwardly from the generally cylindrical portion. The at least one finger is heat-set to remain extended radially inwardly absent an externally applied force thereon. The at least one finger has a free end surrounding a through opening sized for receipt of the wiring harness.

24 Claims, 6 Drawing Sheets

(56) References Cited

U.S. PATENT DOCUMENTS

| | | | | |
|---|---|---|---|---|
| 4,282,397 A | * | 8/1981 | Siedenburg | B29C 61/10 174/92 |
| 4,289,553 A | * | 9/1981 | Nolf | B23P 11/025 156/86 |
| 4,426,413 A | * | 1/1984 | Fentress | H02G 15/18 156/49 |
| 4,472,222 A | * | 9/1984 | Moisson | G02B 6/4476 156/49 |
| 4,656,316 A | * | 4/1987 | Meltsch | H02G 15/1806 174/92 |
| 4,820,561 A | * | 4/1989 | Pithouse | B29C 61/006 428/34.5 |
| 5,002,822 A | * | 3/1991 | Pithouse | B29C 61/006 156/272.2 |
| 6,610,928 B2 | * | 8/2003 | Synder | F16L 59/029 138/149 |
| 2009/0311456 A1 | * | 12/2009 | Harris | F16L 59/022 428/36.1 |

FOREIGN PATENT DOCUMENTS

| | | |
|---|---|---|
| GB | 1470049 A | 4/1977 |
| WO | 2006034027 A2 | 3/2006 |

\* cited by examiner

THERMAL SLEEVE WITH INTEGRAL POSITIONING MEMBER, ASSEMBLY THEREWITH AND METHOD OF CONSTRUCTION THEREOF

CROSS-REFERENCE TO RELATED APPLICATION

This application claims the benefit of U.S. Provisional Application Ser. No. 62/189,097, filed Jul. 6, 2015, which is incorporated herein by reference in its entirety.

BACKGROUND OF THE INVENTION

1. Technical Field

This invention relates generally to tubular sleeve assemblies that provide thermal protection to an electronic object contained therein, and more particularly to a tubular sleeve assembly including a positioning member to maintain the assembly in a selectively releasable, fixed position about the electronic object contained therein.

2. Related Art

Sensors used in automotive applications, such as oxygen sensors which provide data to control engine operation and performance, are often mounted within the engine compartment of a vehicle where they are subject to harsh environmental elements including intense radiant heat, sources of abrasion and vibration during vehicle operation. Due to the harsh environmental elements, it is advantageous, and in many cases a requirement, to cover the relatively delicate, temperature sensitive sensors with protective sleeving in an effort to dampen vibration, provide protection against abrasion and shield radiant heat from reaching the sensor. Such sleeves generally comprise an elongated, cylindrical tube extending between opposite, open free ends. The cylindrical tube includes a damping inner layer of a nonwoven material, for example, polyester felt and a reflective outer layer comprising, for example, an aluminum foil layer laminated to an outer surface of the inner layer.

Due to the configuration of the aforementioned protective cylindrical sleeve and its harsh environment, it is typically difficult to assemble the sleeve about the sensor in a manner which allows the sleeve to be reliably secured and maintained in a desired position, while at the same time being readily removable for servicing of the sensor. Adhesives, tape and interference fits of an entirety of an inner surface of the cylindrical wall of the sleeve are used to effect attachment, but each of these mechanisms suffer various disadvantages. Adhesive attachment of the sleeve about the sensor, while generally secure, at least initially, permanently attaches the sleeve to the sensor, and thus, complicates servicing the sensor at a future time, and in addition, the adhesives can breakdown over time, thereby causing the sleeve to become dislodged from its desired protective position about the sensor. As a result, while generally effective in its initially bonded position, this method does not allow for easy removal of the sleeve for servicing of the sensor or reuse of the sleeve, as it requires destroying the bond joint of the adhesive. In addition, tape and interference fits can be unreliable in view of the heat and vibration encountered within the engine compartment, with tapes further being particularly burdensome to apply, and friction fits of an entirety of a sleeve inner surface suffer from variances in component tolerances, and difficulty of assembly, particularly if the interference is too great, or if the sleeve needs to traverse increased diameter obstacles along the path of assembly, such as a connector, for example.

Further mechanisms are also known, such as using end caps made from separate materials from the tubular sleeve to position the sleeve; however, this method requires assembly of multiple components to one another in construction of the sleeve, thereby adding complexity and cost to the manufacture and assembly of the insulative sleeve.

SUMMARY OF THE INVENTION

In accordance with one aspect of the invention, a thermal sleeve for protecting an electronic member connected to a wiring harness is provided. The thermal sleeve includes a tubular heat-settable nonwoven inner layer having a generally cylindrical portion and an outer surface extending along a longitudinal central axis between opposite open ends. A reflective outer layer is disposed about the outer surface. At least one finger of the heat-settable nonwoven inner layer extends radially inwardly from the generally cylindrical portion. The at least one finger is heat-set to remain extended radially inwardly absent an externally applied force thereon. The at least one finger has a free end surrounding a through opening sized for receipt of the wiring harness.

In accordance with another aspect of the invention, the at least one finger includes a plurality of fingers.

In accordance with another aspect of the invention, the reflective outer layer can be spiral wrapped about the outer surface.

In accordance with another aspect of the invention, the reflective outer layer can be cigarette wrapped about the outer surface.

In accordance with another aspect of the invention, the reflective outer layer can be bonded to the outer surface.

In accordance with another aspect of the invention, the reflective outer layer extends over the at least one finger.

In accordance with another aspect of the invention, a solidified resinous material can be disposed on the nonwoven layer of the at least one finger.

In accordance with another aspect of the invention, a rigid layer of material can be bonded to the nonwoven layer of the at least one finger with the nonwoven layer being sandwiched between the reflective outer layer and the rigid layer of material.

In accordance with another aspect of the invention, the rigid layer of material can be formed of plastic.

In accordance with another aspect of the invention, the at least one finger can include a plurality of fingers and the rigid layer of material can be formed having a plurality of slits aligned with spaces between the fingers.

In accordance with another aspect of the invention, the at least one finger can be provided as a single finger having a plurality of overlapping folded regions.

In accordance with another aspect of the invention, a method of constructing a sleeve for protecting an electronic member connected to a wiring harness is provided. The method includes forming a tubular heat-settable nonwoven inner layer having a generally cylindrical portion and an outer surface extending along a longitudinal central axis between opposite open ends; fixing a reflective outer about the outer surface; and heat-setting at least one finger of the heat-settable nonwoven inner layer to extend radially inwardly from the cylindrical portion and establishing a through opening with a free end of the at least one finger for receipt of the wiring harness in an interference fit therein.

In accordance with another aspect of the invention, the method can further include forming a plurality of the at least one finger.

In accordance with another aspect of the invention, the method can further include forming the plurality fingers after the heat-setting step.

In accordance with another aspect of the invention, the method can further include forming the plurality fingers before the heat-setting step.

In accordance with another aspect of the invention, the method can further include establishing the through opening after heat-setting the at least one finger.

In accordance with another aspect of the invention, the method can further include disposing a resinous layer on the heat-settable nonwoven inner layer of the at least one finger.

In accordance with another aspect of the invention, the method can further include sandwiching the nonwoven layer of the at least one finger between the reflective outer layer and an inner rigid layer of material.

In accordance with another aspect of the invention, the method can further include forming the inner rigid layer of material having generally the same shape as the at least one finger.

In accordance with another aspect of the invention, the method can further include forming the inner rigid layer of material from plastic.

BRIEF DESCRIPTION OF THE DRAWINGS

These and other features and advantages of the present invention will become more readily appreciated when considered in connection with the following detailed description of presently preferred embodiments and best mode, appended claims and accompanying drawings, in which:

DETAILED DESCRIPTION OF PREFERRED EMBODIMENTS

Figure 1A:
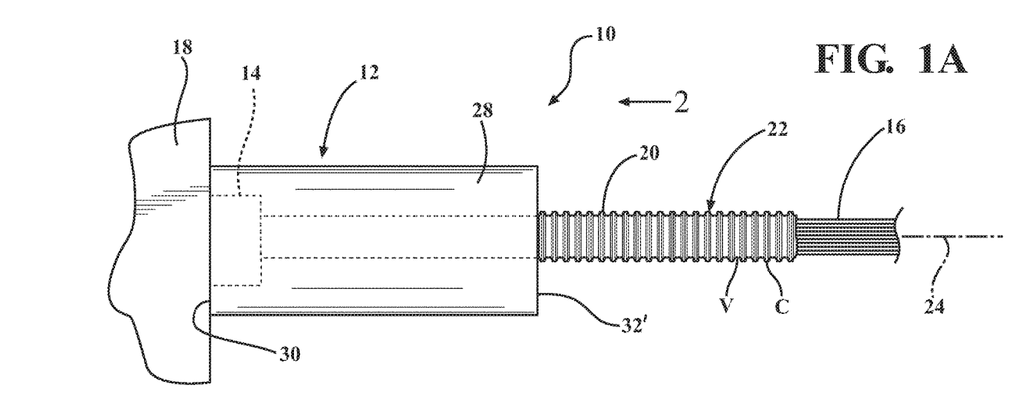
FIG. 1A is a schematic side view of an assembly constructed in accordance with one aspect of the invention for protecting an electrical component.
Figure 1B:
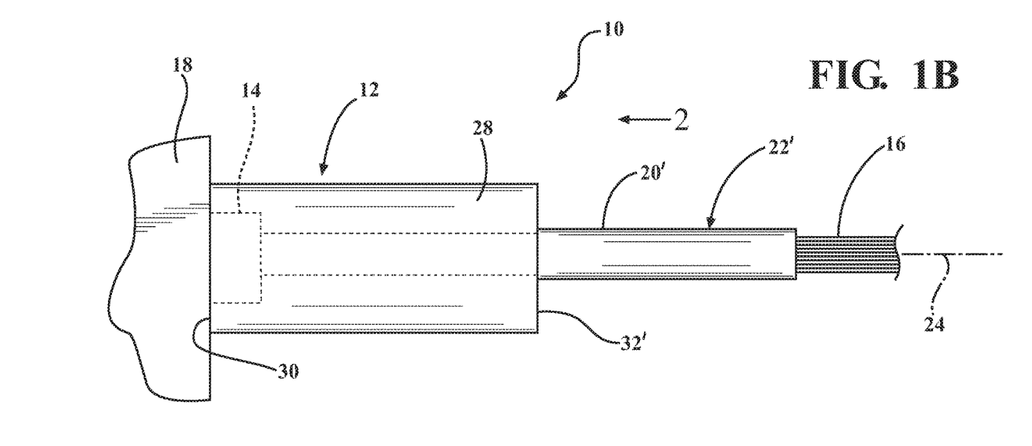
FIG. 1B is a schematic side view of an assembly constructed in accordance with another aspect of the invention for protecting an electrical component.

Referring in more detail to the drawings, FIGS. 1A-1B each show an assembly 10, including a thermal protective sleeve including an integral position member, referred to hereafter simply as sleeve 12, constructed in accordance with one aspect of the invention. The sleeve 12 is used, as least in part, to protect an electrical member 14 contained at least in part therein, such as sensor, against the effects of extreme radiant heat, abrasion, contamination and vibration. The sensor 14 is shown connected to an end of a wire harness 16 on an engine component 18 of a vehicle. The wire harness 16 can be provided as a bundle of exposed, insulated wires, or as a bundle of insulated wires enclosed within an outer protective sleeve, also referred to as tube 20 (FIG. 1A), 20' (FIG. 1B), wherein the tube 20, 20' can have a corrugated or convolute outer surface 22 (FIG. 1A), or generally smooth outer surface 22' (FIG. 1B), by way of example and without limitation. The sleeve 12 is configured for slidable movement along a longitudinal axis 24 of the wire harness 16 and tube 20, 20', if provided, to bring the sleeve 12 into its desired protective position about the sensor 14. The sleeve 12 is further configured, via an integral positioning member made as one-piece of material with the sleeve 12, as discussed in further detail below, to remain fixed in the protective position until desired to selectively slide the sleeve 12 away from its protective position, such as may be desired to service the sensor 14. The sleeve 12 remains in its protective position during use via frictional engagement of the positioning member with the wires 16 or tube 20, 20' thereof, without need of secondary fasteners, such as tape or adhesives, and thus, assembly 10 is made simple and cost effective.

Figure 2A:
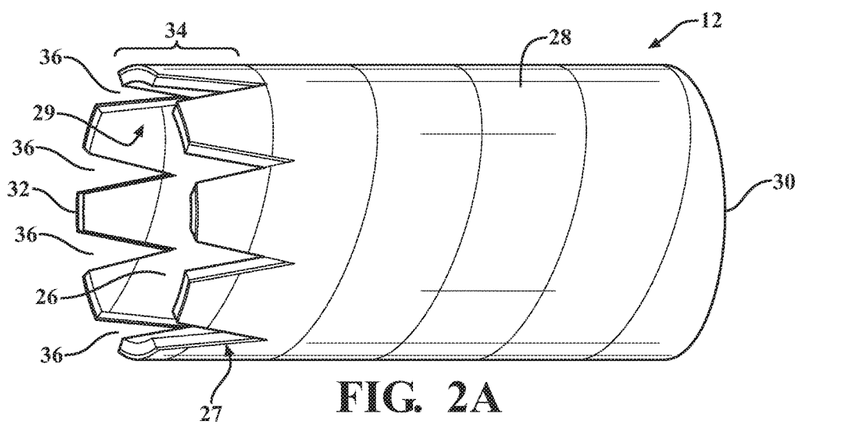
FIG. 2A is a schematic isometric view of the thermal sleeve in accordance with one aspect of the invention of FIGS. 1A-1B shown in a partially constructed state.
Figure 2B:
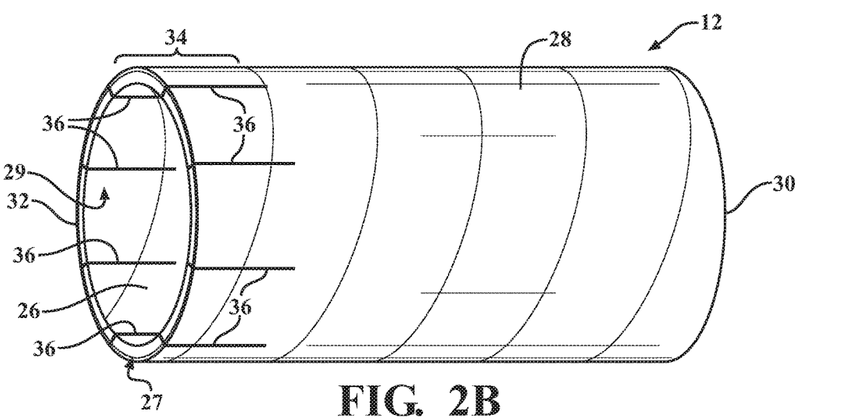
FIG. 2B is a schematic isometric view of the thermal sleeve in accordance with another aspect of the invention of FIGS. 1A-1B shown in a partially constructed state.

The sleeve 12 can be constructed having any desired length. The sleeve 12, as shown in partially constructed embodiments of FIGS. 2A-2C and respective finished embodiments of FIGS. 5A-5C, has a nonwoven inner layer 26 and a reflective outer layer 28. The inner layer 26, in accordance with one aspect of the invention, is constructed of a heat-formable nonwoven material, and can be constructed having any desired wall thicknesses (t), depending on the nature and severity of heat exposure in the intended environment. The nonwoven material forming the inner layer 26 is formed including heat-settable fibers, such as heat-settable low melt fibers including either monofilaments and/or bi-component fibers. The low melt fibers can be mixed with standard thermoplastic fibers and/or fiberglass and/or natural fibers of hemp, jute, Keflex, or the like. The low melt fibers at least partially melt at a temperature lower than the remaining fibers when heat treated in a heat-setting process, whereupon the low melt fibers take on a solidified, heat-set configuration, thereby biasing the inner layer 26 and outer layer 28 to take on and retain a heat-set shape. If bi-component fibers are provided as low melt fibers, they can be provided having a core of a standard thermoplastic material, such as polyethylene terephthalate (PET), for example, with an outer sheath of polypropylene, polyethylene, or low melt polyester, for example. The standard thermoplastic fibers can be provided as any thermoplastic fiber, such as nylon or PET, for example, and act in part to provide the desired density and thickness (t) to the inner layer 26, as desired, thereby providing additional thermal protection and rigidity to the sleeve 12, while also being relatively inexpensive compared to the heat-settable fibers. Accordingly, the inner layer 26 is constructed having a suitable thickness (t) and density of mechanically intertwined, or otherwise bonded, non-woven standard thermoplastic fibers and low melt fibers to obtain the desired physical properties, depending on the application, while also being heat-settable into a desired shape.

The outer layer 28 is provided to reflect extreme radiant heat typical of an engine compartment, including temperatures generated by an exhaust system. The outer layer 28 can be formed of any suitable metal material, including a foil layer of aluminum or other desired metals. The foil outer layer 28 is relatively thin, thereby allowing the sleeve 12 to remain flexible over meandering paths and corners. The outer layer 28 is disposed about an outer surface 27 of the inner layer 26, and can be spiral wrapped or cigarette wrapped about the nonwoven inner layer 26, as desired. Any suitable, heat resistant adhesive can be used to facilitate bonding the outer layer 28 to the inner layer 26, if desired.

Figure 2C:
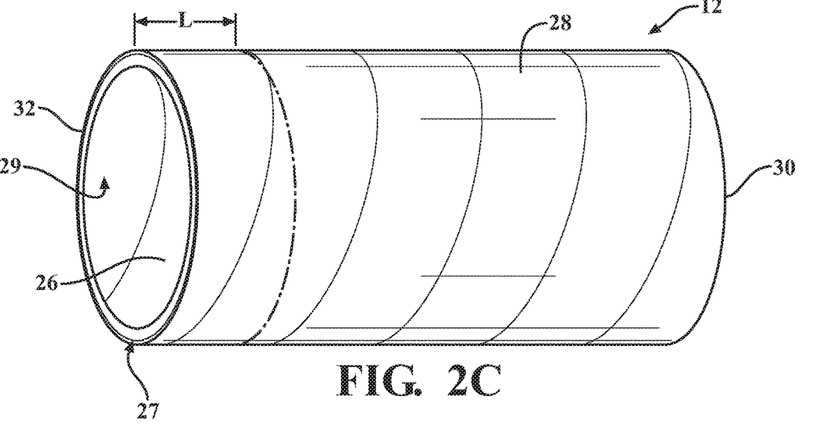
FIG. 2C is a schematic isometric view of the thermal sleeve in accordance with another aspect of the invention of FIGS. 1A-1B shown in a partially constructed state.
Figures 2D, 3A:
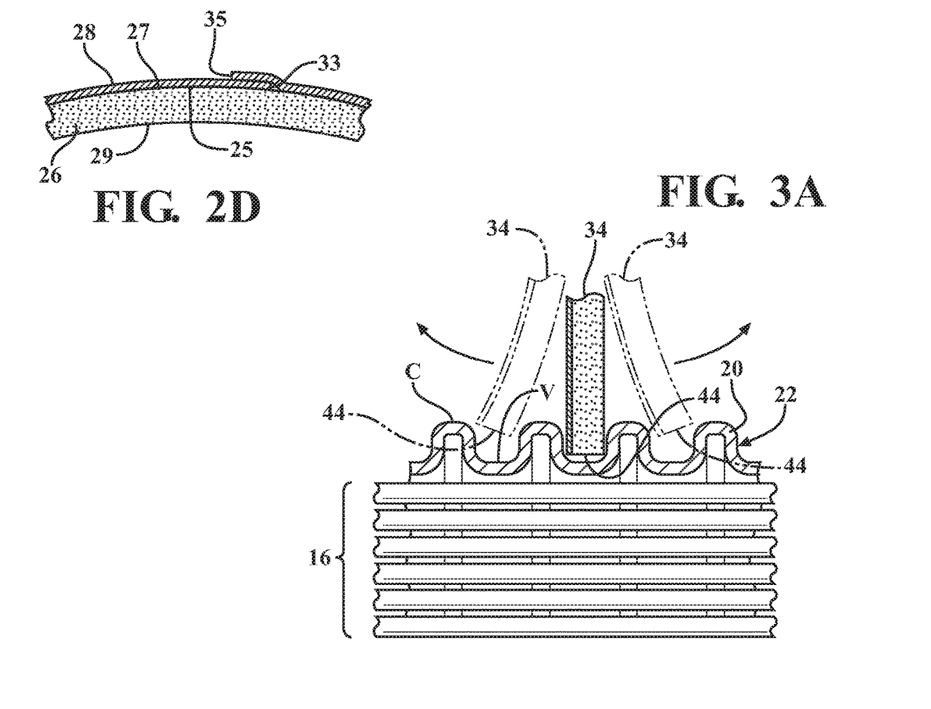
FIG. 2D is a partial cross-sectional end view of the thermal sleeve in accordance with another aspect of the invention of FIGS. 1A-1B.
FIG. 3A is a partial cross-sectional side view of the thermal sleeve and elongate member of FIG. 3 showing a finger in phantom as it deflects axial during relative sliding movement between the thermal sleeve and elongate member.
Figure 3:
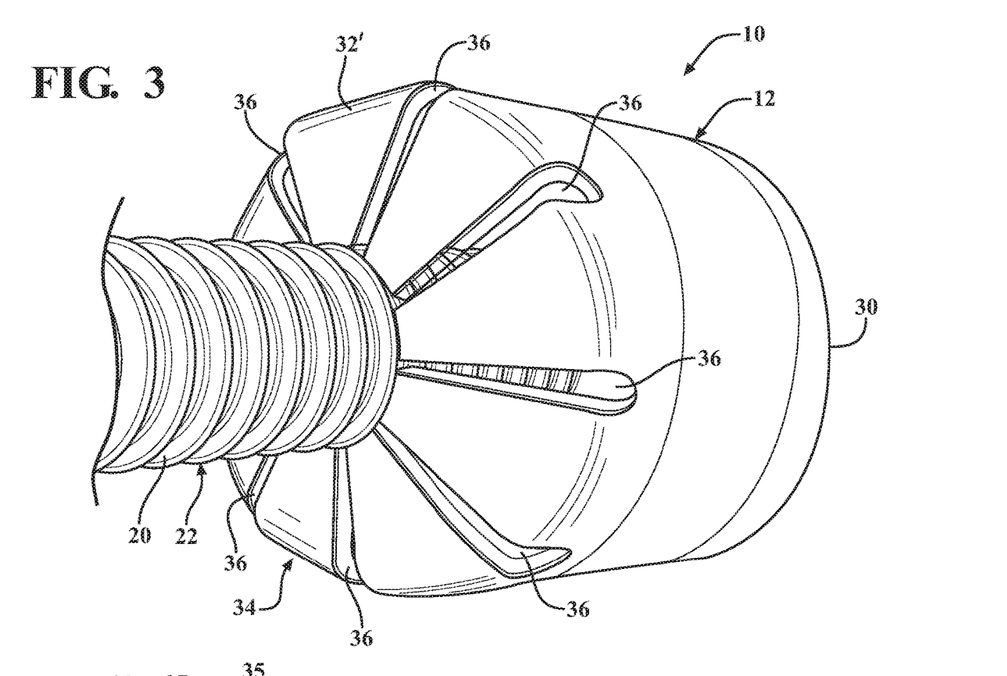
FIG. 3 is an isometric view of the assembly looking generally along the arrow 2 of FIG. 1A.
Figure 4:
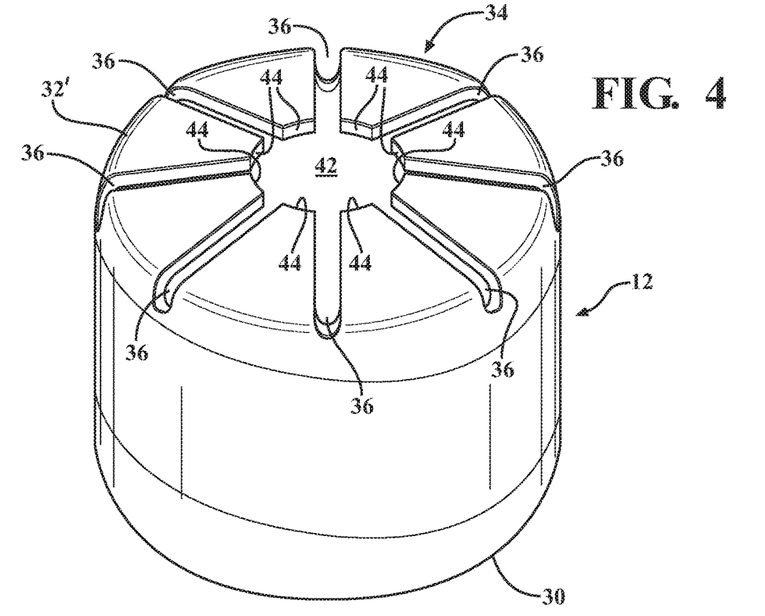
FIG. 4 is an isometric end view of the thermal sleeve of FIG. 2A shown in a finished state.
Figure 5A:
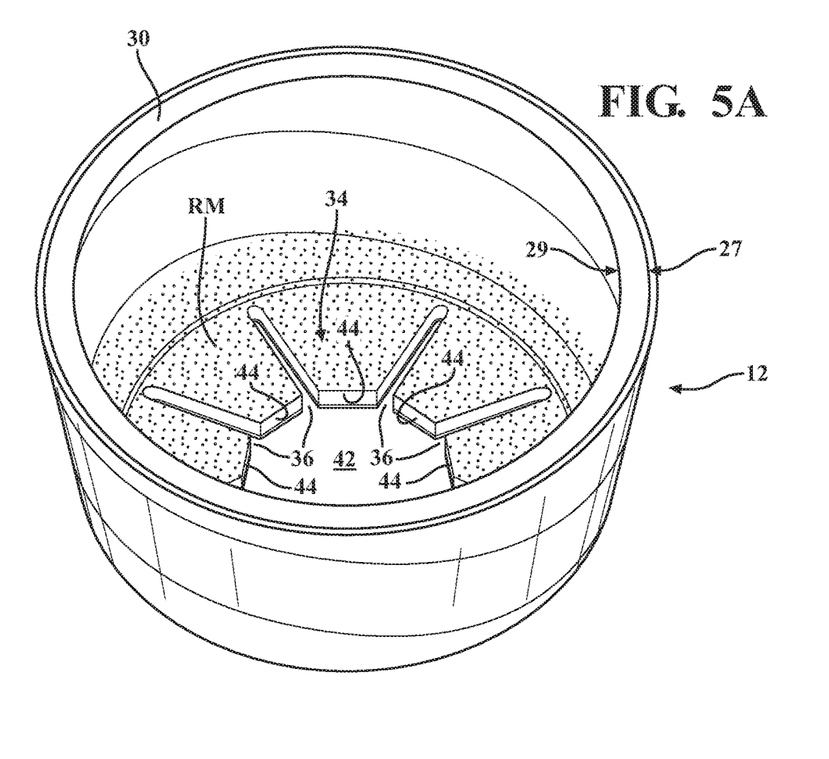
FIG. 5A is an isometric view of an opposite end of the thermal sleeve of FIG. 4.
Figure 5B:
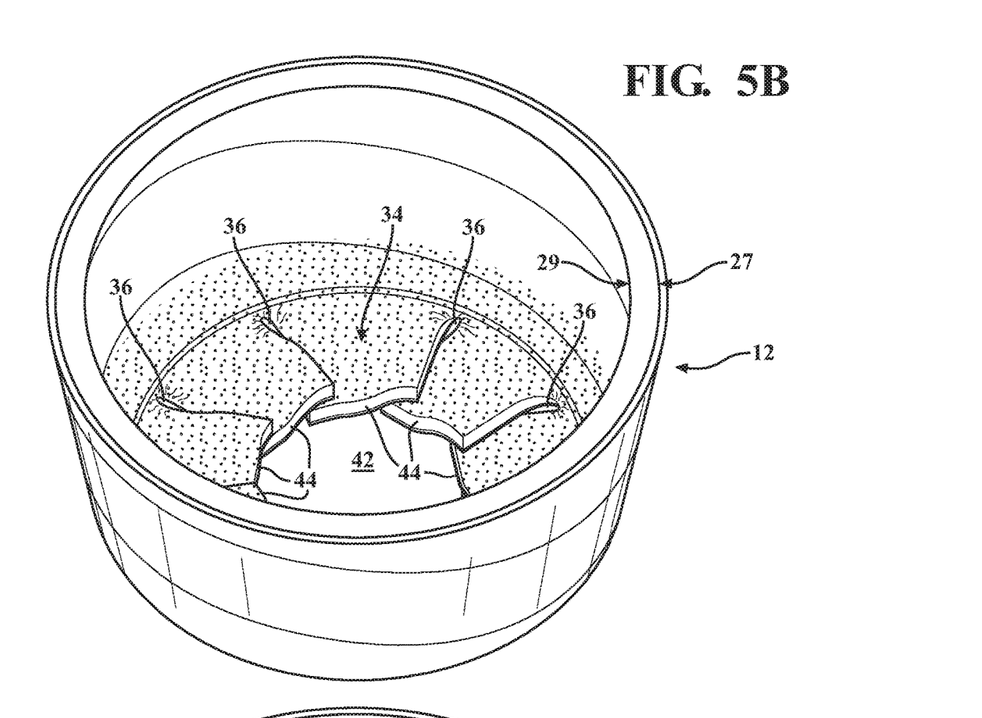
FIG. 5B is view similar to FIG. 5A of the thermal sleeve of FIG. 2B shown in a finished state.
Figure 5C:
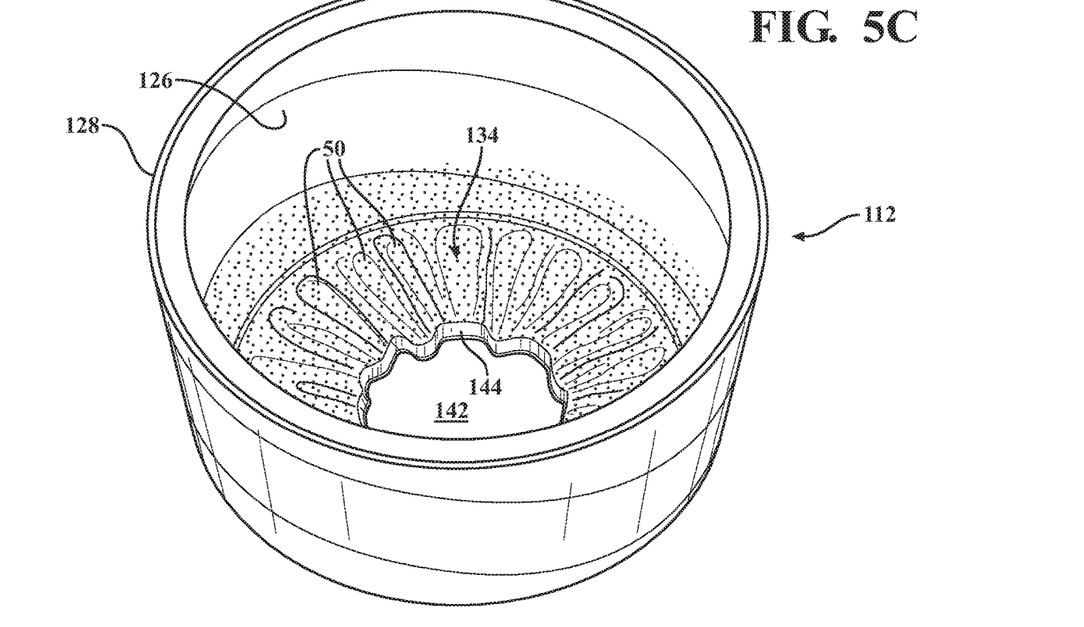
FIG. 5C is view similar to FIG. 5A of the thermal sleeve of FIG. 2C shown in a finished state.
Figure 6:
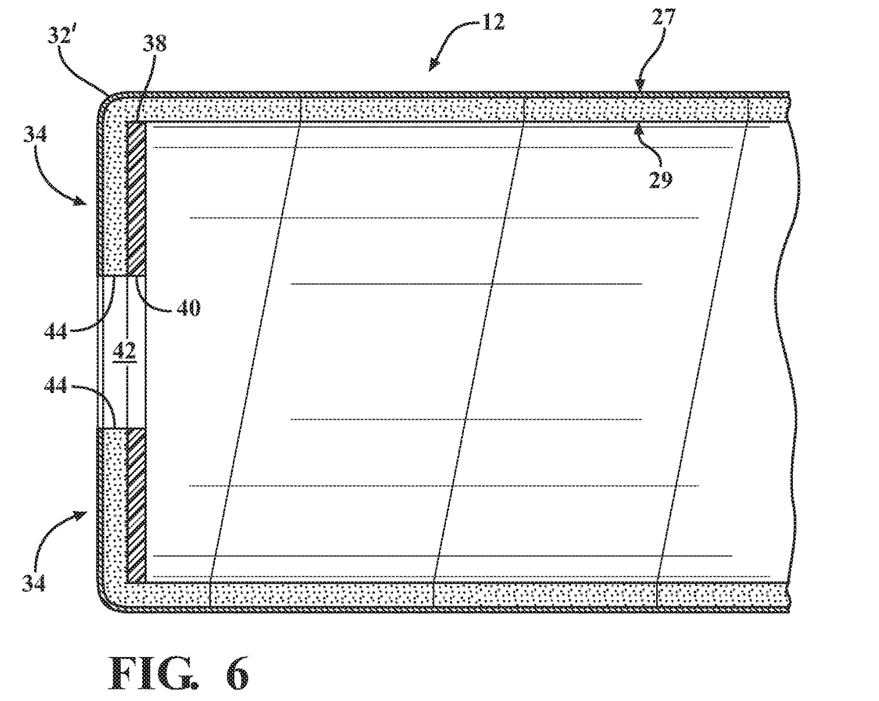
FIG. 6 is a cross-sectional view of a thermal sleeve constructed in accordance with yet another aspect of the invention.
Figure 7:
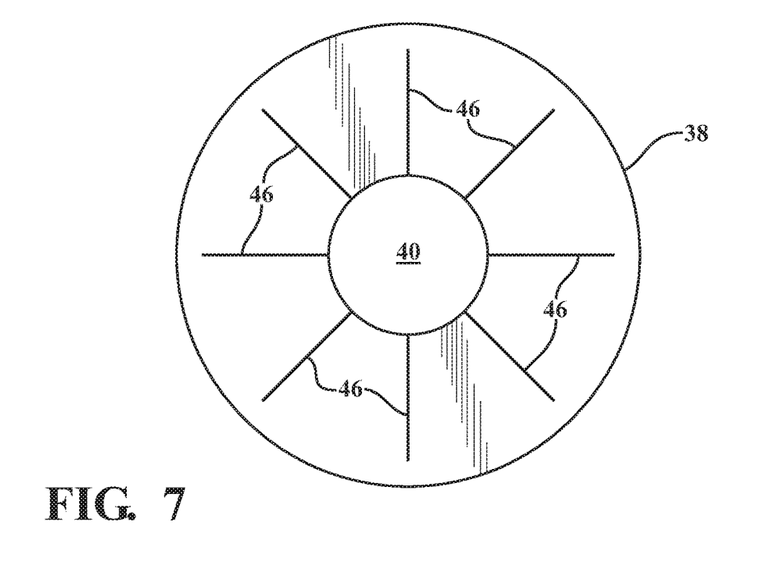
FIG. 7 is a plan view of a support member of the thermal sleeve of FIG. 6.

In accordance with one presently preferred method of constructing the sleeve 12, the nonwoven inner layer 26 is formed as a circumferentially continuous tubular wall, such as by being spiral wrapped, wherein the opposite edges can be brought into flush abutting relation with one another, thereby forming a butt joint 25 (FIG. 2D), to form smooth cylindrical outer and inner surfaces 27, 29 extending between opposite open ends 30, 32. Then, the foil outer layer 28 can be wrapped about, in spiral or cigarette fashion, wherein the foil layer 28 can have opposite edges 33, 35 brought into overlapping relation with one another, and can be mechanically fixed or bonded to the outer surface 27 of the inner layer 26. Then, integral fingers 34, also referred to as positioning members, end projections or locating and retention features, can be formed. In one embodiment, the fingers 34 can be formed in a cutting operation, whereupon some of the inner layer 26 and outer layer 28 is cut via any suitable cutting process to form slits or spaces 36 between adjacent fingers 34. The spaces 36, by way of example and without limitation, are shown as being generally V-shaped in FIG. 2A, though any desired shaped can be formed, thereby facilitating a subsequent folding operation, wherein the fingers 34 are folded radially inwardly to point generally toward one another and subsequently heat-set (FIGS. 3, 4, 5A). For example, as shown in another embodiment, rather than having V-shaped notches formed between adjacent fingers 34, the slits 36 can be formed as straight or substantially straight slits (FIG. 2B), thereby forming generally rectangular fingers 34, whereupon the fingers 34 can then be folded radially inwardly and subsequently heat-set (FIG. 5B). In this embodiment, it can be seen that the individual fingers 34 overlap one another along their radially extending edges, which can further act to provide enhanced protection to the sensor 14. Further yet, rather than forming slits or otherwise cutting the sleeve wall to form individual fingers, a desired uncut length (L; FIG. 2C) of an end region of the sleeve wall can be folded radially inwardly without first cutting or slitting, whereupon a single, circumferentially extending finger 34 can be formed, having accordion-like, folded overlapping regions as a result of not having slits (FIG. 5C). The folding operation can be performed by first disposing the tubular wall on a mandrel, and then folding the plurality of fingers 34 or single finger 34, depending on the construction desired, over an end of the mandrel to bring the inner layer 26 into abutment with a generally flat end of the mandrel. Then, with the finger(s) 34 in the folded position, sufficient heat can be applied to the inner layer 26 to cause the inner layer, at least within the region including the finger(s) 34, to take on a heat-set. The heat can be applied via a heatable mandrel and/or via an external source of heat. Accordingly, the finger(s) 34 are heat-shaped to remain or substantially remain in the "as folded" position, thereby providing the sleeve 12 with a remaining cylindrical portion extending from one end 30 to the location, a newly formed end 32' of the cylindrical portion of the sleeve 12, where the finger(s) 34 are bent radially inwardly. In accordance with another aspect of the invention, as shown in FIGS. 5A-5C, it is contemplated that a resinous material RM could be applied to the inner layer 26, at least on the region of the inner layer 26 forming the fingers 34, or to the entirety of the inner layer 26, if desired, to facilitate providing the material of the fingers 34 with the desired stiffness, rigidity, resiliency and flexibility desired to optimally function as retention and retaining members. Further yet, as shown in FIGS. 6 and 7, a separate support member in the form of a reinforcing layer of material, such as a plastic material, by way of example and without limitation, of desired thickness, resiliency and flexibility, such as a generally circular disc 38, having through opening 40 sized and shaped similarly to an opening 42 formed by free ends 44 of the fingers 34, could be bonded inside the sleeve 12 in abutment with the inner layer 26 of the fingers 34. If provided, it is contemplated that the circular disc 38 would have slits 46 formed therein, as shown, with the slits 46 being arranged to register in axially and radially aligned relation with the slits or spaces 36 to allow the fingers 34 to remain resiliently flexible axially inwardly and axially outwardly along the axis 24 during assembly and removal of the sleeve 12 along the wire harness 16. Of course, it should be recognized the slits 46 can be formed to take on the same shape as the slits 36 formed between the fingers 34, as desired.

Upon completing the heat-setting operation, the sleeve 12 can be removed from the mandrel, wherein the one-piece sleeve 12 is provided, without having to fasten other components thereto in secondary operations, having a cylindrical portion extending from the open end 30 to an end location 32' where the fingers 34 are folded radially inwardly, without need of secondary fasteners to join the fingers 34 to the sleeve 12.

In use, the sleeve 12 can be easily slid over the wire harness 16 or tube 20 thereof, whereupon ends 44 of the fingers 34 engage and flex axially against the wires harness 16 or tube 20. A predetermined amount of friction and interference between the finger end(s) 44 and the wire harness 16 or tube 20 can be provided by sizing the opening 42 bounded by the finger end(s) 44 in construction. As shown generally in FIG. 3A, with the fingers 34 being flexible and resilient, the fingers 34 are readily biased slightly axially via friction or interference with the wire harness 16 or tube 20 to flex axially away from the sleeve end 30 during installation and axially toward the sleeve end 30 during removal, such as may be required in service. If a tube 20 is provided as a corrugate tube (FIG. 1A), the fingers 34 can be biased to flex axially over annular crests C during installation and removal, and can be constructed to take on a predetermined thickness to be received within annular valleys V of the corrugations to facilitate maintaining the sleeve 12 in its intended "in use" position about the sensor 14.

In FIG. 5C, a sleeve 112 constructed in accordance with another aspect of the invention is shown, wherein the same reference numerals, offset by a factor of 100, are used to identify like features. The sleeve 112 has an inner layer 126 and an outer layer 128 constructed of the same materials discussed above for the sleeve 12. In contrast to the sleeve 12, a single finger 134 is folded radially inwardly, however, the free end 144 of the finger 134, rather than forming an opening for receipt of the wires 16 or tube 20 as folded, can be formed via a subsequent cutting operation, such as die cutting via a circular punch, or any desired outer peripherally shaped punch. As such, the through opening 142 can be formed having a precisely sized and shaped configuration, whether circular or other configuration, thereby resulting in a precision amount of interference between a free end 144 of the finger 134. As such, it should be recognized that a single, circumferentially continuous finger 134 can be folded radially inwardly, and then the opening 142 can be cut. Of course, this same mechanism for form the central opening can be used if a plurality of fingers 134 are formed and folded radially inwardly. If a single finger 134 is formed, the finger 134 has a plurality of overlapping folded regions 50 formed by the material of the finger 134. Further yet, it is contemplated that upon folding the single finger 134 or plurality of fingers 134 radially inwardly, the finished shape of individual fingers 134 can be subsequently formed in a cutting operation, in addition to the cutting operation used in forming the opening 142.

Obviously, in light of the above teachings, many modifications and variations of the present invention are possible. It is, therefore, to be understood that within the scope of the appended claims, the invention may be practiced otherwise than as specifically described.

What is claimed is:

1. A thermal sleeve for protecting an electronic member connected to a wiring harness, comprising:
    a tubular heat-settable nonwoven inner layer having a generally cylindrical portion and an outer surface extending along a longitudinal central axis between opposite open ends;
    a reflective outer layer disposed about said outer surface; and
    at least one finger of said heat-settable nonwoven inner layer extending radially inwardly from said generally cylindrical portion, said at least one finger being substantially planar and heat-set to remain extending radially inwardly absent an externally applied force thereon and having a free end surrounding a through opening sized for receipt of the wiring harness; and
    wherein said at least one finger includes a plurality of fingers with slits extending between adjacent fingers.

2. The thermal sleeve of claim 1 wherein said reflective outer layer is cigarette wrapped about said outer surface.

3. The thermal sleeve of claim 1 wherein said reflective outer layer is bonded to said outer surface.

4. The thermal sleeve of claim 1 wherein said reflective outer layer extends over said at least one finger.

5. The thermal sleeve of claim 1 further including a solidified resinous material on said nonwoven layer of said at least one finger.

6. The thermal sleeve of claim 1 further including a rigid layer of material bonded to said nonwoven layer of said at least one finger with said nonwoven layer being sandwiched between said reflective outer layer and said rigid layer of material.

7. The thermal sleeve of claim 6 wherein said rigid layer of material is plastic.

8. The thermal sleeve of claim 1 wherein said at least one finger has a plurality of overlapping folded regions.

9. A thermal sleeve for protecting an electronic member connected to a wiring harness, comprising:
    a tubular heat-settable nonwoven inner layer having a generally cylindrical portion and an outer surface extending along a longitudinal central axis between opposite open ends;
    a reflective outer layer disposed about said outer surface;
    at least one finger of said heat-settable nonwoven inner layer extending radially inwardly from said generally cylindrical portion, said at least one finger being heat-set to remain extending radially inwardly absent an externally applied force thereon and having a free end surrounding a through opening sized for receipt of the wiring harness; and
    wherein said reflective outer layer is spiral wrapped about said outer surface.

10. A thermal sleeve for protecting an electronic member connected to a wiring harness, comprising:
    a tubular heat-settable nonwoven inner layer having a generally cylindrical portion and an outer surface extending along a longitudinal central axis between opposite open ends;
    a reflective outer layer disposed about said outer surface;
    at least one finger of said heat-settable nonwoven inner layer extending radially inwardly from said generally cylindrical portion, said at least one finger being heat-set to remain extending radially inwardly absent an externally applied force thereon and having a free end surrounding a through opening sized for receipt of the wiring harness;
    further including a rigid layer of material bonded to said nonwoven layer of said at least one finger with said nonwoven layer being sandwiched between said reflective outer layer and said rigid layer of material; and
    wherein said at least one finger includes a plurality of fingers and said rigid layer of material has a plurality of slits aligned with spaces between said fingers.

11. A thermal sleeve assembly, comprising:
    a wire harness;
    a tubular heat-settable nonwoven inner layer having a generally cylindrical portion along a longitudinal central axis about said wire harness and having an outer surface extending between opposite open ends;
    a reflective outer layer disposed about said outer surface;
    at least one finger of said heat-settable nonwoven inner layer extending radially inwardly from said generally cylindrical portion, said at least one finger being heat-set to remain extending radially inwardly absent an externally applied force thereon and having a free end surrounding a through opening sized for receipt of said wiring harness; and
    wherein said wiring harness has a convolute outer surface including peaks and valleys and said at least one finger sized for receipt in one of said valleys.

12. The thermal sleeve assembly of claim 11 wherein said at least one finger engages an outer surface of said wiring harness.

13. The thermal sleeve assembly of claim 11 wherein said at least one finger includes a plurality of fingers with slits formed between said fingers, wherein said fingers are sized for simultaneous receipt in a common one of said valleys.

14. The thermal sleeve assembly of claim 11 further including a solidified resinous material on said nonwoven layer of said at least one finger.

15. The thermal sleeve assembly of claim 11 further including a rigid layer of material abutting said nonwoven layer of said at least one finger with said nonwoven layer being sandwiched between said reflective outer layer and said rigid layer of material.

16. The thermal sleeve assembly of claim 11 wherein said at least one finger has a plurality of overlapping folded regions.

17. The thermal sleeve assembly of claim 11 wherein said at least one finger includes a plurality of fingers with slits extending between adjacent fingers.

18. A method of constructing a sleeve for protecting an electronic member connected to a wiring harness, comprising:
   forming a tubular heat-settable nonwoven inner layer having a generally cylindrical portion and an outer surface extending along a longitudinal central axis between opposite open ends;
   fixing a reflective outer about the outer surface;
   heat-setting at least one finger of said heat-settable nonwoven inner layer to extend radially inwardly from the cylindrical portion and establishing a through opening with a free end of the at least one finger for receipt of the wiring harness in an interference fit therein;
   further including forming a plurality of said at least one finger by forming slits between adjacent fingers; and
   further including forming the plurality fingers after the heat-setting step.

19. The method of claim 18 further including disposing a resinous layer on the heat-settable nonwoven inner layer of the at least one finger.

20. The method of claim 18 further including sandwiching the nonwoven layer of the at least one finger between the reflective outer layer and an inner rigid layer of material.

21. The method of claim 20 further including forming the inner rigid layer of material having generally the same shape as the at least one finger.

22. The method of claim 20 further including forming the inner rigid layer of material from plastic.

23. A method of constructing a sleeve for protecting an electronic member connected to a wiring harness, comprising:
   forming a tubular heat-settable nonwoven inner layer having a generally cylindrical portion and an outer surface extending along a longitudinal central axis between opposite open ends;
   fixing a reflective outer about the outer surface;
   heat-setting at least one finger of said heat-settable nonwoven inner layer to extend radially inwardly from the cylindrical portion and establishing a through opening with a free end of the at least one finger for receipt of the wiring harness in an interference fit therein;
   further including forming a plurality of said at least one finger by forming slits between adjacent fingers; and
   further including forming the plurality fingers before the heat-setting step.

24. A method of constructing a sleeve for protecting an electronic member connected to a wiring harness, comprising:
   forming a tubular heat-settable nonwoven inner layer having a generally cylindrical portion and an outer surface extending along a longitudinal central axis between opposite open ends;
   fixing a reflective outer about the outer surface;
   heat-setting at least one finger of said heat-settable nonwoven inner layer to extend radially inwardly from the cylindrical portion and establishing a through opening with a free end of the at least one finger for receipt of the wiring harness in an interference fit therein; and
   further including establishing the through opening after heat-setting the at least one finger.

* * * * *